(12) United States Patent
Li et al.

(10) Patent No.: US 9,915,819 B2
(45) Date of Patent: Mar. 13, 2018

(54) FIBER-OPTIC METHODS AND DEVICES ENABLING MULTIPHOTON IMAGING WITH IMPROVED SIGNAL TO-NOISE RATIO

(71) Applicant: THE JOHNS HOPKINS UNIVERSITY, Baltimore, MD (US)

(72) Inventors: Xingde Li, Ellicott City, MD (US); Yicong Wu, North Potomac, MD (US); Wenxuan Liang, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/169,917

(22) Filed: Jun. 1, 2016

(65) Prior Publication Data

US 2016/0357008 A1 Dec. 8, 2016

Related U.S. Application Data

(60) Provisional application No. 62/169,712, filed on Jun. 2, 2015.

(51) Int. Cl.

| | |
|---|---|
| *G02B 23/26* | (2006.01) |
| *G02B 23/24* | (2006.01) |
| *G01N 21/64* | (2006.01) |
| *G01N 33/483* | (2006.01) |
| *G02B 21/00* | (2006.01) |
| *G02B 26/10* | (2006.01) |
| *A61B 5/00* | (2006.01) |

(Continued)

(52) U.S. Cl.
CPC .......... *G02B 23/26* (2013.01); *A61B 5/0068* (2013.01); *A61B 5/0084* (2013.01); *G01N 21/636* (2013.01); *G01N 21/6458* (2013.01); *G01N 33/4833* (2013.01); *G02B 21/0008* (2013.01); *G02B 23/243* (2013.01); *G02B 23/2469* (2013.01); *G02B 26/103* (2013.01); *A61B 1/0017* (2013.01); *G01N 2021/6478* (2013.01); *G01N 2021/6484* (2013.01); *G01N 2201/0866* (2013.01); *G01N 2201/10* (2013.01); *G02B 3/0087* (2013.01)

(58) Field of Classification Search
CPC .. G02B 23/26; G02B 21/0008; G02B 23/243; G02B 23/2469; G02B 26/103; G01N 21/6458; G01N 33/4833; A61B 1/00096; A61B 1/04; A61B 1/0661; A61B 1/07
See application file for complete search history.

(56) References Cited

U.S. PATENT DOCUMENTS

| | | | |
|---|---|---|---|
| 4,435,040 A * | 3/1984 | Cohen | C03C 13/045 385/127 |
| 2004/0254474 A1* | 12/2004 | Seibel | A61B 5/0062 600/473 |

(Continued)

*Primary Examiner* — Christine Sung
(74) *Attorney, Agent, or Firm* — Johns Hopkins Technology Ventures

(57) ABSTRACT

The present invention is directed to a fiber optic device that enables multiphoton imaging with improved signal-to-noise ratio having a single piece of double-clad fiber (DCF). The device also includes all components for focusing, scanning and signal collection within an endomicroscope probe of 2.1 mm outer diameter (OD). The unprecedented imaging capability of this miniature endomicroscope is demonstrated herein via both ex vivo and in vivo experiments.

21 Claims, 4 Drawing Sheets

(51) Int. Cl.
*G01N 21/63* (2006.01)
*G02B 3/00* (2006.01)
*A61B 1/00* (2006.01)

(56) References Cited

U.S. PATENT DOCUMENTS

| | | | |
|---|---|---|---|
| 2007/0213618 A1* | 9/2007 | Li | A61B 1/00096 600/476 |
| 2010/0210937 A1* | 8/2010 | Tearney | A61B 5/0066 600/424 |
| 2017/0010456 A1* | 1/2017 | Gopinath | G02B 23/243 |

* cited by examiner

FIBER-OPTIC METHODS AND DEVICES ENABLING MULTIPHOTON IMAGING WITH IMPROVED SIGNAL TO-NOISE RATIO

CROSS REFERENCE TO RELATED APPLICATIONS

This application claims the benefit of U.S. Provisional Patent Application No. 62/169,712, filed Jun. 2, 2015, which is incorporated by reference herein, in its entirety.

GOVERNMENT SUPPORT

This invention was made with government support under CA153023 awarded by the National Institutes of Health. The government has certain rights in the invention.

FIELD OF THE INVENTION

The present invention relates generally to imaging. More particularly the present invention relates to fiber optic methods and devices enabling multiphoton imaging with improved signal-to-noise ratio.

BACKGROUND OF THE INVENTION

With inherent optical sectioning capability, deeper penetration and reduced out-of-focus photodamage, multiphoton microscopy technologies, especially two-photon fluorescence (TPF) and second harmonic generation (SHG), have been widely used in biological and biomedical studies. However, their benefits to in vivo studies and clinical applications are limited, since the conventional bench-top laser-scanning microscope (LSM) lacks access to tissues deep inside animal bodies. To extend the applicability of these high-resolution powerful imaging modalities, a miniature flexible endomicroscope with imaging capability comparable to standard LSMs is highly desirable, and recent years have witnessed a plethora of different endomicroscope designs.

Irrespective of the variety of optical and mechanical designs, one central challenge to build an endomicroscope for practical clinical usage is to achieve as high system detection sensitivity as possible. Here the detection sensitivity is quantitatively defined as the achievable signal-to-noise ratio (SNR) per unit incident power per unit fluorophore concentration, which is basically an inclusive metric of the system's capability to acquire high-SNR two-photon images. For clinical applications, high detection sensitivity is particularly critical as: 1) it is preferable to utilize just endogenous fluorophores, e.g. nicotinamide adenine dinucleotide (NADH) and flavin adenine dinucleotide (FAD), and/or structural proteins, e.g. collagen fibers, all generally existing in lower abundance and exhibiting much smaller two-photon cross sections compared with exogenous dyes or fluorescent proteins; 2) the maximal applicable incident power is limited due to safety concerns. Previous endomicroscopy prototypes, although demonstrating great potential, generally suffered from inadequate sensitivity, as either sample staining or very high excitation power (~70 mW) was required for adequate image quality.

The difficulty to achieve high detection sensitivity is partially aggravated by the miniaturization. Several previous designs employed two optical fibers: one single-mode fiber for excitation light delivery and one large-diameter multimode fiber for signal collection. Such dual-fiber scheme, although favorable for collecting more nonlinear emission, usually led to a probe size too large to go through the access channels (~2.8-4 mm diameter) of commercial gastroscopes or colonoscopes.

It would therefore be advantageous to provide a smaller probe that provides high quality images and still fits within the access channels of commercial scopes.

SUMMARY

According to a first aspect of the present invention a device includes a housing. The device also includes a single light guide configured for delivery of excitation light and collection of emission light disposed within the housing. Further, the device includes a piezoelectric tube (PZT) configured to function as an actuator disposed at a first end of the housing, and an achromatic objective lens disposed at a second end of the housing.

In accordance with an aspect of the present invention the single light guide takes the form an optical fiber. The single light guide can have a single or multiple single-mode cores and multiple claddings, with the core(s) for delivery of excitation light to the sample, and at least one cladding (and the core(s)) for collection of emission light from the sample. The single light guide can have a pure silica core, a potassium doped silica sore, and a hollow core. The single light guide includes an optical fiber having at least one single-mode core and one cladding also including a low refractive index coating.

In accordance with another aspect of the present invention, the objective lens includes low or no chromatic aberration and is configured to have a wavelength range of interest to improve the efficiency of coupling the emission light back into the fiber. The achromatic objective lens is configured for collecting the emission light with a short wavelength (e.g. 350-600 nm) mainly generated from the focal volume of the excitation light of a long wavelength (e.g. 750-1060 nm). The achromatic objective lens includes a miniature compound lens further having multi-elements of different refractive index profiles (including GRIN lenses/glasses) and/or curvatures to correct chromatic aberration and field flatness for a scanning input imaging beam. The achromatic objective lens takes the form of a miniature compound lens with a diffraction element/mask to compensate the chromatic aberration and thus reduce the longitudinal focal shift, while maintaining a high numerical aperture (and thus resolution) and small size.

In accordance with yet another aspect of the present invention, the device includes a built-in mechanism to perform 2D and 3D beam scanning. The built-in mechanism to perform 2D and 3D beam scanning can take the form of a PZT actuated 2D fiber scanner, an MEMS actuated 2D or 3D fiber scanner, a built-in depth scanner, and a mechanical scanner consisting of a compressed spring and shape-memory alloy wires to translate parts of the focusing optics relative to the rest of the probe. The built-in mechanism is equipped with corresponding drive and control electronics. A short pulsed light source can be used as the excitation light source. A dispersion management unit is configured to compensate the dispersion of the fiber and other optics in the system to achieve short pulses and good emission signal production. The dispersion management unit can take the form of a photonic bandgap fiber, a pair of gratings, a pair of prisms, and a grating-lens pair. The device can include a mechanism to separate the emission light from the excitation light. The mechanism to separate the emission light from the excitation light can take the form of a dichroic mirror. A light detector can be configured to detect the emission light, electronics to condition and acquire the signal, and electronics to digitize and store the signal in digital form. The light detector takes the form of a photomultiplier tube. The device can also include a control device, imaging beam scanner drive, data acquisition, display and storage unit to control and synchronize the drive signals and data acquisition, digitize the data, process the data, and store data. Optics configured to couple the light between free space and optical fiber can also be included.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and:

FIGS. 4A and 4B illustrate intrinsic TPF images of mouse small intestine mucosa simultaneously acquired in two spectral channels (the same as in the ex vivo case). The focal depths were ~3 μm (a) and ~16 μm (b) below the corresponding villi tip. FIGS. 4C-4H illustrate two-photon autofluorescence from the renal tubule cells (417-477 nm emission band, false-colored in green), and TPF from fluorescein (496-680 nm emission band, false-colored in red), acquired ~4 (FIG. 4C), ~7 (FIG. 4D), ~10 (FIG. 4E), ~13 (FIG. 4F), ~16 (FIG. 4G), and ~40 (h) minutes following tail-vein injection of fluorescein-conjugated dextran tracer. Excitation condition used for all subfigures here was 30 mW at 750 nm, and 2 frames were averaged. Scale bar: 10 μm.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a fiber optic device that enables multiphoton imaging with improved signal-to-noise ratio having a single piece of double-clad fiber (DCF). The device also includes all components for focusing, scanning and signal collection within an endomicroscope probe of 2.1 mm outer diameter (OD). The unprecedented imaging capability of this miniature endomicroscope is demonstrated herein via both ex vivo and in vivo experiments.

To apply the powerful multiphoton microscopy technologies to in vivo clinical practice, flexible fiber-optic endomicroscopes have been explored recently to enable direct access of internal organs. To truly fit and benefit clinical applications, endomicroscopy utilizing only endogenous fluorophores and/or structural proteins is preferred. Thus, besides the pursuit of miniaturization, another necessary attribute is high detection sensitivity, which has been lacking in previous reports of miniature endomicroscope designs. The present invention is based on a solution to several critical performance-limiting issues, including nonlinear background emission of the pulse-delivering optical fiber and focal shift of the micro-objective lens, and proposed corresponding solutions. Within a compact probe diameter (~2.1 mm), the newly-developed endomicroscope of the present invention achieves unprecedented detection sensitivity, being capable of clearly visualizing subcellular structures using only intrinsic two-photon signal and moderate excitation power. Imaging results demonstrated the promising potential of the device to realize in vivo optical biopsy in clinical environments.

Figures 1A, 1B, 1C, 1D:
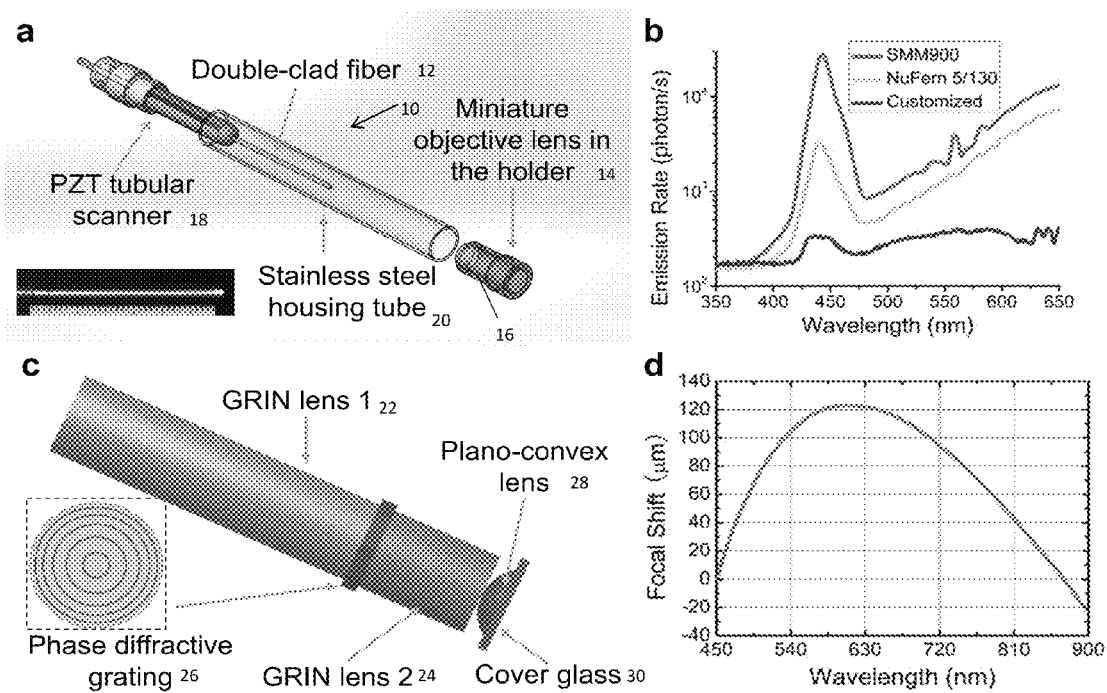
FIG. 1A illustrates a perspective view of an endomicroscope according to the present invention with an inset photograph showing the actual dimension (each fine ruler scale is 1 mm).
FIG. 1B illustrates a graphical view of a nonlinear background emission rate from three kinds of DCF plotted against wavelength.
FIG. 1C illustrates a perspective view of the micro-objective lens, with a front view of the phase diffractive grating.
FIG. 1D illustrates a graphical view of simulated back focal shift of the micro-objective lens.

The mechanical assembly of the endomicroscope probe of the present invention is illustrated in FIG. 1A. The device 10 includes a single-mode core double-clad fiber (DCF) 12. The DCF is used to deliver femtosecond laser pulses. The device 10 also includes a micro-objective lens 14 to focus and to collect the emission photons. The miniature objective lens is disposed within the holder 16. The large inner-clad of the DCF 12 guides the signal back to the proximal end of the device 10 for detection. A tubular piezoactuator 18 is utilized to resonantly vibrate the fiber cantilever into a spiral-scanning pattern. The components are all housed within a stainless steel housing tube 20, wherein the stainless steel housing tube has a diameter small enough to be disposed within a typical scope. It should be noted that these components are exemplary and any suitable component known to or conceivable to one of skill in the art for executing the purpose could also be used.

Associated with the device of the present invention, the first challenge comes from the nonlinear background emission from the DCF core. Commercially available passive DCFs generally employ germanium dioxide ($GeO_2$) dopant to raise the refractive index of the fiber core. It turns out that the dopant also renders the fiber core two-photon active, giving out a detectable level of both TPF and SHG signal when femtosecond laser pulses are propagating through it. Previous research has attributed the source of SHG to the broken inversion symmetry of silica established by self-organization of charge-transfer excitons of Ge centers, and the source of TPF to oxygen-deficient defects caused by $GeO_2$ dopant. The background spectra of two commonly-used commercial DCFs is characterized as: SM-GDF-5/130 from NuFern and SMM900 from Fibercore; both were adopted in previous endomicroscope designs. By coupling femtosecond laser pulses (890-nm central wavelength), into the DCF core and detecting backward-propagating nonlinear emission out of the same end surface, the spectra of nonlinear background emission are measurable (FIG. 1B, top two curves). The curves show that both spectra exhibit a relatively narrow SHG peak and a broad fluorescence component extending up to 600 nm. Such nonlinear background emission is very hard to eliminate. First, its broad spectrum overlaps largely with that of typical intrinsic TPF and SHG signal, thus optical filters are helpless. Secondly, the background fluorescence photons occur in a random fashion (Poisson stochastic process), so that the noise level varies dramatically pixel by pixel. Even with the average background level subtracted, the significant fluctuation can still overshadow typical levels of intrinsic TPF and SHG signal, thus deteriorating the overall image SNR and the system detection sensitivity.

Because both TPF and SHG background have the root in germanium dopant, this problem is solved by customizing a DCF 12 with a pure silica core, which ensures low two-photon luminescence and reduces the chance of quasi-phase matching for SHG generation. To form the waveguide structure, the clad region is doped with index-decreasing fluorine dopant. With the same setup, the background emission spectrum from the customized DCF was also measured (FIG. 1B, bottom curve). Compared with the two commercial DCFs, the background noise from the customized DCF features a similar spectrum shape, but the absolute spectrum intensity is much lower. By numerically integrating the spectrum curves, the total average emission rate of background photons from the two commercial fibers is ~35 times and ~15 times, respectively, higher than the customized DCF. With Poisson distribution assumed, the fluctuation of background noise level is reduced by ~5.9 and ~3.9 times, which lowers the level of minimal detectable signal and proportionally enhances the system detection sensitivity.

The second approach to enhance the system detection sensitivity is to increase the signal collection capability. A multiphoton endomicroscope relies on a micro-objective lens both to focus the excitation light into the tissue, and to collect the emission photons back onto the fiber end surface. Unfortunately, common micro-lenses such as gradient-index (GRIN) lenses generally exhibit considerable positive chromatic aberration, which leads to a significant longitudinal focal shift of the emission light with respective to the fiber end surface (where the excitation wavelength would focus). Specifically, as the two-photon emission wavelength (e.g. 400-600 nm) is much shorter than the excitation wavelength (e.g. 800-950 nm), the back-focus of emission light will fall in front of the fiber tip, resulting in significant collection loss of emission photons even with a large-inner-clad DCF. To reduce such focal shift, micro-objective lenses with 2-3 aspherical and/or doublet lens elements have been devised; however, either the focal shift is still as large as 1 mm (for 400-nm-wavelength emission) or the focusing NA is sacrificed. Further complicated designs integrating even more lens elements can potentially yield better performance, but the overall length might grow too long to fit in a flexible, compact endomicroscope probe.

To effectively correct chromatic aberration while maintaining compactness, the device of the present invention includes an integrated diffractive optical elements (DOE) into the lens design, as illustrated in FIG. 1C). The device 10 includes two GRIN lenses 22, 24 that sandwich a phase diffractive grating 26. The device 10 also includes a plano-convex lens 28 with a cover glass 30. With chromatic dispersion property complementary to common refractive lenses, DOE has been adopted in eyepiece and camera lens designs. The DOE used here was a multi-layer phase diffraction grating, which is concentric with the grating interval getting denser near the periphery (inset in FIG. 1C). Longer-wavelength light, with larger diffraction angle, will focus closer to the DOE (complementary chromatic dispersion); by tuning the grating interval, the wave front can be shaped. This DOE is sandwiched between two GRIN lenses, with the first GRIN lens (~¼ pitch) collimating the diverging beam out of the DCF core, and the second GRIN lens (<¼ pitch) pre-focusing the beam. Further in front is a high-NA plano-convex lens for tight focusing, and the working distance (WD) is ~200 µm in water. By optimizing the refractive index profile of the two GRIN lenses and the interval pattern of the phase diffraction grating, both spherical and chromatic aberrations were minimized. All refractive and diffractive elements are finally encapsulated and fixed within a protective stainless-steel sheath (1.4-mm OD×6.5-mm length).

The final focal shift is simulated over a broad wavelength range, as illustrated in FIG. 1D, from which it is seen that the maximal focal shift is well controlled within 150 µm. Given the design NAs of the micro-objective lens (~0.16 image NA and ~0.80 object NA), geometrical calculation estimates that the ballistic signal photons, as long as collected by the micro-objective lens, will hit the fiber end surface within a circle of ~49 µm diameter; thus they will be readily collected by the 185-µm-diameter 0.35-NA inner clad of the customized DCF. The "over-sized" high-NA inner clad and the well-controlled micro-objective-lens focal shift are more crucial for imaging practical scattering tissues, where lots of non-ballistic signal photons will enter the micro-objective lens with large skew angles and are harder to collect. To experimentally verify and evaluate the collection efficiency improvement, the customized lens was compared with the compound lens developed. By mounting them to the same endomicroscope probe, mouse tail tendon was imaged for comparing SHG collection, and a uniform fluorescein phantom for TPF collection. The comparison reveals that the customized micro-objective lens can enhance SHG and TPF signal strength by ~2.5 and ~2.0 times, respectively. Note that these two ratios were obtained using the customized large-inner-clad DCF, so the overall collection efficiency enhancement enabled by customizing both the DCF and the micro-objective lens should be even higher.

Figures 2A, 2B, 2C:
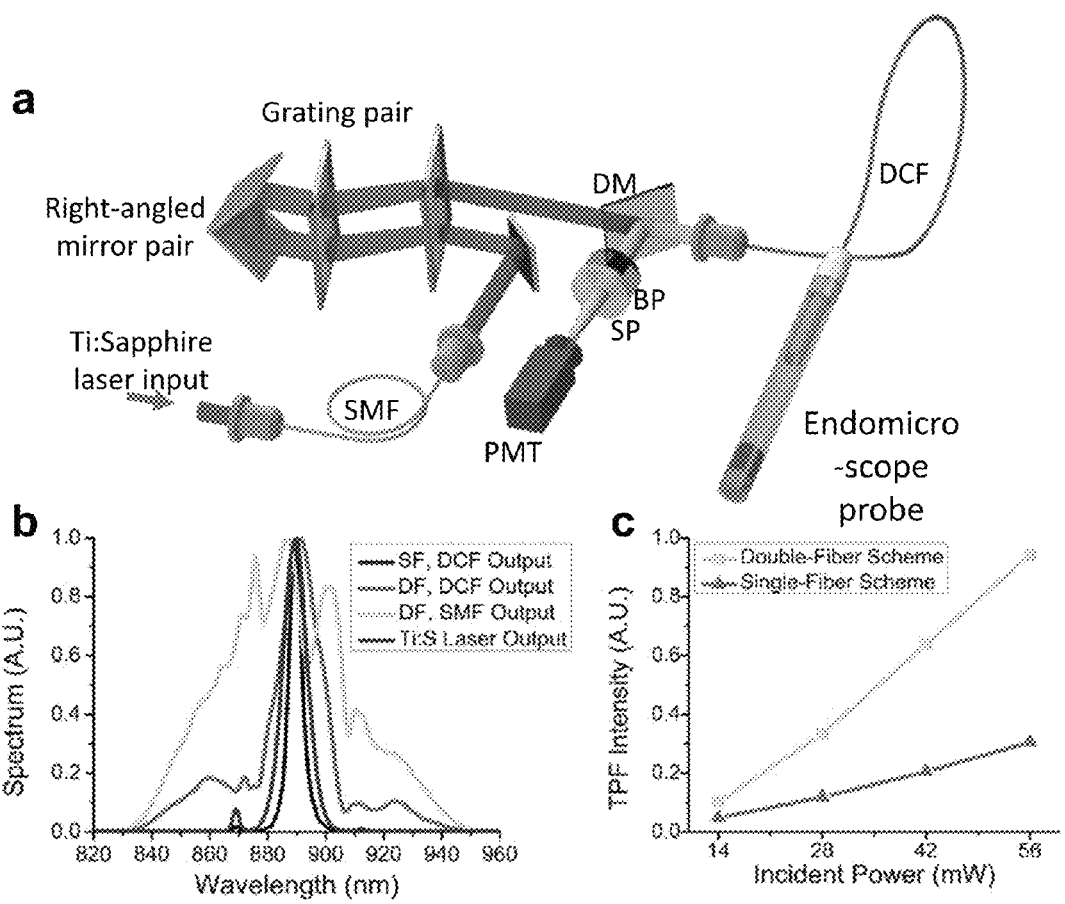
FIG. 2A illustrates a schematic diagram of a system according to an embodiment of the present invention. BP: band-pass optical filter. DM: dichroic mirror. PMT: photomultiplier tube. SP: short-pass optical filter.
FIG. 2B illustrates a graphical view of a pulse spectrum evolution (890-nm central wavelength) through the whole system for both single-fiber (SF) and double-fiber (DF) compensation schemes. SPM-induced spectrum narrowing of negatively-chirped pulses was observed under single-fiber scheme by comparing the output (black) to the laser spectrum (blue), and under double-fiber scheme by comparing the DCF output spectrum (red) to the SMF output spectrum (green).
FIG. 2C illustrates a graphical view of a TPF intensity difference under the two compensation schemes at different power levels.

The final approach incorporated into a device of the present invention is to enhance the system detection sensitivity is to maintain a short temporal pulse width, so that more nonlinear emission photons per given incident power can be excited. It is well-known that femtosecond laser pulses, when propagating through fiber core, are subject to temporal broadening induced by both linear dispersion and nonlinear effects. Previous research has revealed that the primary nonlinear effect, self-phase modulation (SPM), acts to narrow the spectrum of negatively chirped femtosecond pulses; thus with linear pre-chirping only, pulse broadening is "inevitable" due to the time-bandwidth product limit. The present invention incorporates spectral compensation in addition to negative pre-chirping to maintain a narrow pulse width. As shown in the system schematic, illustrated in FIG. 2A, un-chirped laser pulses are first launched into a piece of single-mode fiber (SMF) to achieve spectral broadening via the SPM effect. Then the pulses are negatively chirped and coupled into the DCF core, where both temporal pulse width and spectral bandwidth get compressed during propagation; one example of pulse spectrum evolution is illustrated in FIG. 2B. Numerical simulation has revealed that the optimal pulse width appears when the negative group delay imposed by the grating pair just cancels the total positive group delay induced in both fibers, and the output pulse width is not sensitive to varying power level. An autocorrelator was used to verify that the full width at half maximum (FWHM) of the intensity autocorrelation function (ACF) of output pulses stayed ~120 fs with the average propagation power in DCF ranging from 14 to 56 mW. In contrast, when only grating-pair pre-chirping is used, the intensity ACF FWHM of output pulses grew from ~420 fs to ~720 fs when the propagation power increased from 14 to 56 mW. Quantitative phantom experiments showed that the double-fiber scheme could promote the TPF intensity by ~2-3 times, as illustrated in FIG. 2C.

Figures 3A, 3B, 3C, 3D, 3E, 3F:
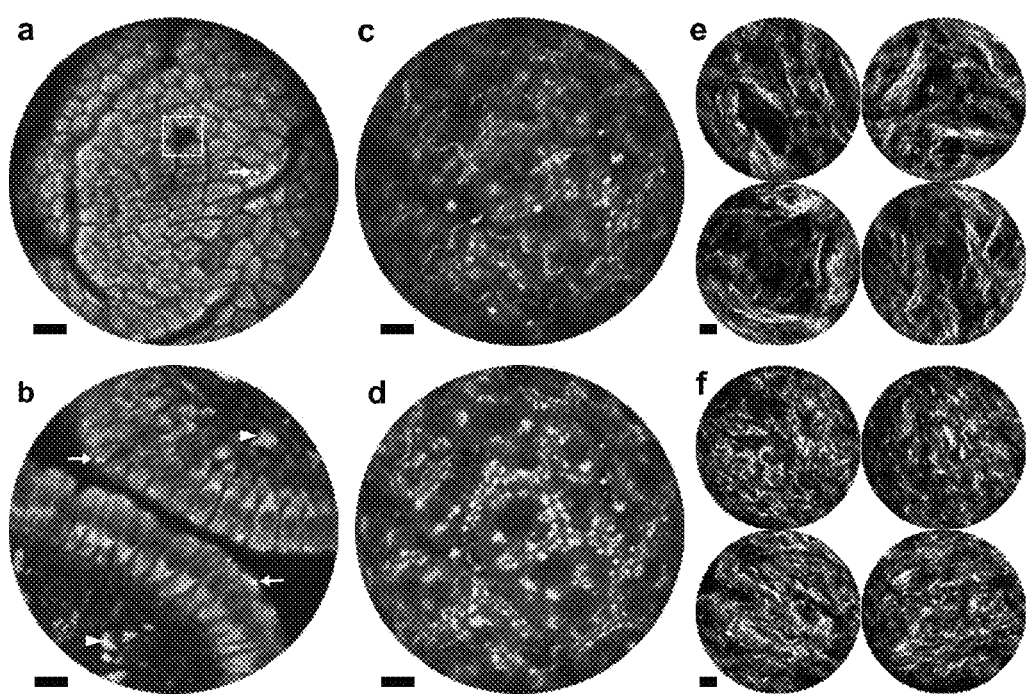
FIGS. 3A and 3B illustrate an image view of intrinsic TPF images of mouse small intestine mucosa simultaneously acquired into two spectral channels: 417-477 nm (false-colored in green) and 496-680 nm (false-colored in red).
FIGS. 3C and 3D illustrate image views of an overlay of intrinsic TPF and SHG image acquired from mouse liver tissue in two spectral channels: 496-680 nm (false-colored in green) and 435-455 nm (SHG signal, false-colored in red).
FIGS. 3E and 3F illustrate SHG images of cervical tissue sections form mifepristone-treated PTB mouse models (e) and normal pregnant mice at gestation day 15 (f); each panel includes four sub-figures acquired from different locations to better reveal the morphological difference in collagen structure. Excitation condition used for each panel was: 30 mW at 750 nm FIGS. 3A, 3B, and 3C, 30 mW at 890 nm FIG. 3D, and 40 mW at 890 nm FIGS. 3E and 3F 4 frames were averaged for FIGS. 3A, 3B, and 3C 5 frames for FIG. 3D, and 10 frames for FIGS. 3D, 3E, and 3F. Scale bar: 10 μm.

As illustrated in FIGS. 3A-3F, representative intrinsic TPF and SHG images acquired from unstained ex vivo mouse tissues. FIGS. 3A and 3bB are TPF images of mouse small intestine mucosa at different penetration depths. In FIG. 3A, with the focus tuned just beneath the tip of one intestinal villus, epithelia cells (mostly enterocytes) show up in a mosaic pattern and green-yellowish false color, matching the emission spectra of NADH and FAD. The mucus-secreting goblet cells can also be found as dark patches scattered among the bright enterocytes (dash box). By moving the focal plane ~20 μm deeper, FIG. 3B shows a cross-sectional view of intestine villi lined up by individual enterocytes; the nuclei appear dark compared to the cytoplasm which mitochondria are abundant. Within the villus lamina propria, antigen-presenting cells (APCs) containing many lysosomes show up as bright reddish granules (arrowheads). Lysosomes are also important for enterocytes' absorption function, and they preferably accumulate in the apical cytoplasm, as revealed by the yellowish punctate granules in both FIGS. 3A and 3B (arrows).

FIG. 3C and FIG. 3D show the overlay of intrinsic TPF and SHG signal acquired from the same lateral location on a mouse liver. With the focal plane going ~20 μm deeper from FIG. 3C to 3D, SHG signal (red) from collagen fibers decays while the cytoplasm TPF (green) brightens up, reflecting the three-dimensional interlacing between individual liver cells (most hepatocytes here) and the supporting fine meshwork of reticulin fibers (collagen type III). Noticeable in these two figures are multiple bright granules scattered around in the cytoplasm; these are believed to be lipofuscins, which are known to be autofluorescent and accumulate with cell aging.

Juxtaposed for comparison are SHG images which reveals collagen fibers in cervical tissues from a mifepristone-treated pre-term birth (PTB) mouse model (FIG. 3E) and a normal pregnant mouse at gestation day 15 (FIG. 3F). Morphologically, the collagen structure is clearly more porous in PTB group, which reflects the pre-mature cervical ripening induced by mifepristone.

During in vivo imaging of live animals, the tissues are generally subject to respiration-induced bulky motion and/or gastrointestinal peristalsis. Therefore, to avoid introducing severe motion-induced blurriness, the number of frames that can be averaged is limited. In this case, with the exceptional detection sensitivity, the endomicroscope of the present invention can still capture clear subcellular structures.

Figures 4A, 4B, 4C, 4D, 4E, 4F, 4G, 4H:
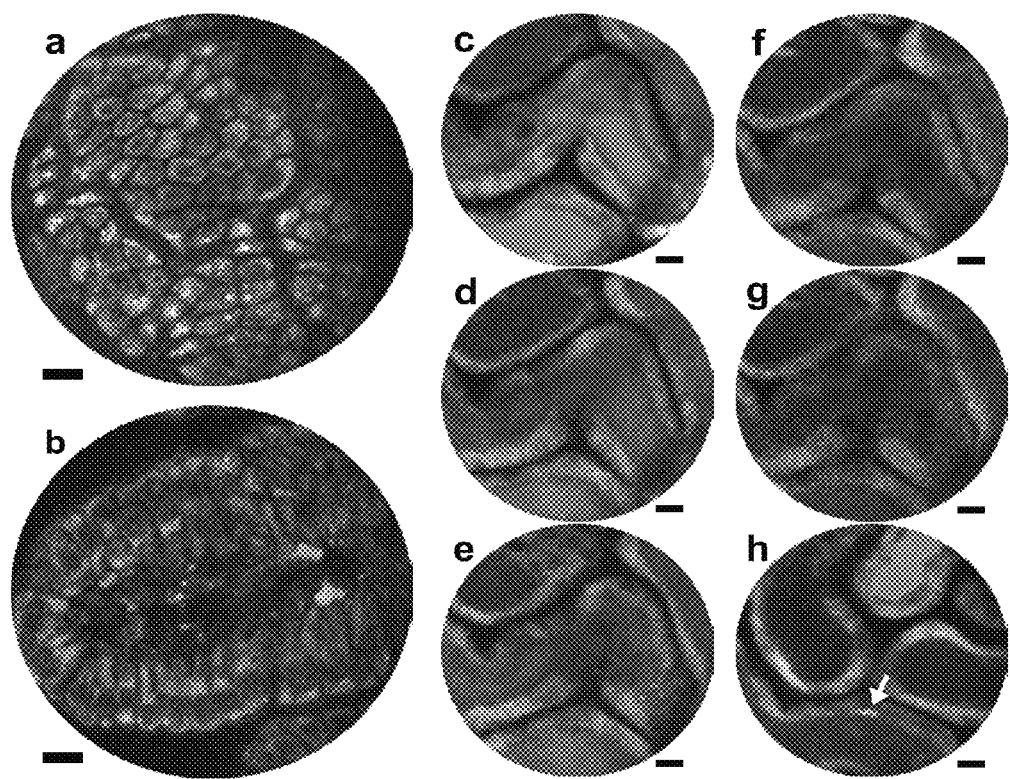
FIGS. 4A-4H illustrate representative in vivo TPF endomicroscopy images. More particularly.

Intrinsic TPF imaging of mouse small intestine mucosa was tested in vivo, with the same excitation power as in the ex vivo case but less frames to average (two-frame averaging for static images in FIGS. 4A and 4B, and single-frame for the supplementary movie). In the resultant images, similar subcellular structures, e.g. reddish APCs inside the lamina propria and yellowish punctate granules in the apical cytoplasm of enterocytes, are still distinctly visualized. One highly desirable feature of in vivo study is the potential to monitor dynamic information from functioning organs or tissues. To demonstrate this, prolonged TPF imaging was conducted of mouse kidney in vivo, and to visualize the fluid transport in renal tubules, fluorescein-conjugated dextran with molecular weight of ~3,000-5,000 (Sigma-Aldrich Co.) was tail-vein injected. As shown in FIG. 4C to 4H, segments of renal tubules are delineated by the cytoplasm autofluorescence (green-colored) of epithelial cells, and tubular fluid dynamic can be tracked by the fluorescein signal (red-colored). Following dextran injection (~4 minutes later), fluorescein signal quickly emerged in the proximal renal tubules (FIG. 4C), and then decays with time (FIG. 4C to 4G). At ~40 minutes post injection, most fluorescein signal was cleared from proximal tubules and concentrated inside the distal tubules (FIG. 4H); some dextran tracer was internalized by proximal tubule cells, as revealed by the yellowish punctate granules (arrows).

In summary, with significantly enhanced detection sensitivity, the endomicroscope of the present invention can clearly visualize subcellular structures with only intrinsic TPF and SHG signal using moderate excitation power (30~40 mW), thus demonstrating a strong potential for a wide range of clinical applications. If appropriate exogenous fluorophores could be employed for some cases, dynamic changes would be captured on top of the autofluorescence context, yielding valuable functional information.

It has been shown that two-photon excitation reduces the overall photodamage compared with confocal microscopy; however, nonlinear photodamage within the focal volume can still be harmful. Although the average excitation power used in the exemplary experiments included herein was ~30 mW (except ~40 mW for ex vivo cervical tissue sections), which exceeds the photodamage-free threshold (<10 mW) suggested by previous cell-culture studies, no visible signs of photodamage were noticed during the imaging experiments. Possible explanations include lower focusing NA (~0.6), continuous beam scanning, and relatively higher photodamage tolerance of tissues compared with cell cultures.

The current 2.1-mm OD of the endomicroscope of the present invention can be further decreased in size with better mechanical design, as essentially it is lower-bounded by the piezoelectric tube (1.3-mm OD) and the micro-objective lens (1.4-mm OD). The FOV of the current endomicroscope is ~100 μm in diameter, beyond which vignetting in excitation illumination grows significant. The limited FOV and WD majorly result from the requirement of tight focusing within a small probe OD, and investigation into better optical designs is underway.

Another mechanical factor limiting the flexibility of endomicroscope probe is the rigid-part length (~32 mm), which is currently limited by the total length of fiber cantilever and piezoelectric tube (each ~10 mm long). These two lengths are closely related to the resonant scanning frequency and the scanning range per driving voltage. Although shortening the cantilever can increase the scanning speed, thus potentially diminishing motion artifacts, the extent of shortening should be balanced with decrease in both achievable scanning range and available emission photon budget per frame (assuming the same excitation condition). The best compromise is application-dependent.

Finally, one could have noticed that when comparing the double-fiber pulse-width compensation with the grating-only-single-fiber method, the extent of enhancement in TPF excitation (~2-3 times) was less than the extent of narrowing in the FWHM of pulse intensity ACF (~4-6 times). This discrepancy is attributed to changes in temporal shape and spectral profile of output pulses between these two setups. Especially, in the double-fiber scheme, pulse spectrum is largely broadened, which can exceed the absorption spectrum of fluorophores and thus reduce the excitation efficiency. Further research on how to better manipulate the spectral broadening is worth exploring.

A piezoelectric (PZT) tube with its surface divided into four quadrant electrodes functions as an actuator. Briefly, the DCF is threaded through and anchored to the PZT tube, with its free end serving as a cantilever. By driving the two electrode pairs with appropriate amplitude-modulated sinusoidal waveforms, the fiber tip can resonantly vibrate into open and close spiral scan pattern. With the DCF cantilever set to ~11 mm long, the mechanical resonant frequency is ~1380 Hz. Throughout this paper, 512 circles were acquired to recover one frame, so the single-frame acquisition time is ~0.37 s. The spatial resolution of the endomicroscope (~0.7 μm lateral and ~6.5 μm axial) was estimated by imaging stage-scanned 0.1-μm-diameter fluorescent beads and 1 μm-thickness fluorescent thin film, respectively, and then Gaussian fitting the resultant fluorescent profiles.

The FWHM of the un-chirped pulses from the Ti:Sapphire laser (Chameleon Vision II, Coherent) is ~150 fs. The SMF adopted is also polarization-maintaining (PM780-HP, Thorlabs). The grating pair (600 lines/mm, Wasatch Photonics) adopted here can generate ~−1000 $fs^2$ (~−642 $fs^2$) GDD per millimeter separation for pulses of 890-nm (780-nm) central wavelength. Given the SMF and DCF length (25 cm and 75 cm, respectively), optimal pulse width at 890-nm (780-nm) central wavelength was achieved when the grating pair separation was tuned to ~36 mm (~55 mm). Due to the limited grating transmission efficiency (~80%) and coupling loss, propagation power in the DCF core was ~20% of that in the SMF. Therefore the SPM effect in the DCF was weakened compared to in the SMF, resulting in insufficient spectrum compression, as illustrated in FIG. 2B. Emission signal propagating back through the DCF was first separated from the excitation light by a dichroic mirror (FFF665-Di02-25x36, Semrock), and then passed a short-pass optical filter (FF01-680/SP-25, Semrock) and appropriate fluorescence filter(s) before getting detected by the PMT (H10771P-40, Hamamatsu).

To implement the single-fiber compensation scheme for comparison, the SMF was bypassed, and the grating pair was tuned until the narrowest intensity ACF was obtained for 56-mW propagation power in the DCF. The fluorescent phantom used to compare the TPF intensity was home-made with 10 μM fluorescein distributed uniformly in diluted gelatin solution (~% 10 mass concentration). The phantom was sealed beneath a piece of No. 0 cover glass (~100 μm thick) to avoid dissolution during imaging since the micro-objective lens required water immersion. The fluorescein phantom used for micro-objective lens comparison was prepared in the same way. No visible sign of photobleaching was observed during imaging.

The pure-silica-core DCF was fabricated using the outside vapor deposition (OVD) technology. A core NA of ~0.12 was realized by tuning the fluorine doping concentration in the inner-clad, and single-mode operation was achieved by precisely controlling the core size (~5.5 μm). Similarly, the high inner-clad NA (~0.35) was realized by further tuning the fluorine doping concentration in the outer-clad.

The measurement setup was similar as the system schematic except that the emission signal was sent through a grating-based monochromator (Acton SP2300i, Princeton Instruments) and detected with a PMT (H7422-P50, Hamamatsu) working in photon-counting mode (SPC-150, Becker & Hickl GmbH). The PMT was cooled to ensure a stable dark count rate (<200 photons/s). The emission spectra were characterized at 1-nm interval, and total emission within 12 s was averaged and background-subtracted to give the emission rate. The fiber length (~70 cm) and propagation power (40 mW at 890 nm) were maintained the same for the three pieces of DCF, and the distal DCF end surface was exposed to air.

For ex vivo imaging, the mice were euthanized by carbon dioxide asphyxiation, and then the organs of interest were dissected. The liver lobe was rinsed with phosphate buffered saline (PBS) and then pinned to a homemade wax plate fixed to a Petri dish. PBS was filled into the dish until just immersing the tissue, both to avoid dehydration and to maintain water immersion for the micro-objective lens. The segment of small intestine dissected (~1 cm long) was cut open lengthwise and flushed gently by PBS until no intestinal intents were visible. The intestine segment was then spread on a microscope slide with the mucosa (inner side) facing up and pressed slightly against a piece of No. 0 coverslip to minimize motion artifacts. PBS was diffused between the coverslip and microscope slide to keep the intestine moisturized during imaging.

For in vivo imaging, the mouse was first sedated in an induction chamber with ~5% isoflurane-oxygen mixture gas until adequate anesthesia was assured; then the mouse was moved onto a temperature-controlled heating pad (36° C.) and fitted to a rodent mask to maintain anesthesia with ~2-3% isoflurane-oxygen mixture gas. For small intestine imaging, a small abdominal incision was made, through which small intestine part (jejunum or ileum) was identified. Then a loop of small intestine was carefully dragged out and fixed to a home-built supporting frame without damaging blood vessels running in the mesentery. To access the intestinal mucosa, one short intestine segment (~1 cm) was cut open along the dorsal side with respect to intestinal artery arcades in order to minimize bleeding. Afterwards, cleaning and coverslip were applied similarly as described in the ex vivo case. For kidney imaging, a ~10-mm-long lateral incision was made dorsally to expose one kidney. A small drop of PBS was diffused between the micro-objective lens and kidney surface to maintain water immersion during imaging.

The disclosed technology is a noninvasive (or minimally invasive at most), high-resolution, optical imaging technology. The endomicroscope, which is the key component of the technology, is flexible, potentially disposable, and capable of accessing internal organs (such as gastrointestinal tract etc.) in addition to other easy-to-access organs (such as skin, oral cavity etc.). The technology can visualize tissue microanatomies at cellular and subcellular level, enabling "optical histology" in vivo, in situ and in real time without the need for tissue removal.

The imaging principle is based on multiphoton nonlinear optical imaging, which involves the absorption of two or more photons simultaneously to excite fluorescent or structural or other types of molecules. The conventional platform for performing nonlinear optical imaging is a bench-top microscope. The nonlinear microscopy technology has been proven powerful for basic research by offering subcellular resolution and label-free imaging capability. The bulky size of a microscope, however, has been the hurdle for clinical translation of the nonlinear microscopy technology, particularly for imaging internal organs.

The disclosed endomicroscopy technology enables clinical translation of the above mentioned powerful nonlinear microscopy. In addition, the endomicroscopy technology can also be used as a basic research tool, which would be more flexible and much less expensive than a microscope.

The potential applications include: Tissue Pathology Detection: the endomicroscope can assess tissue histology and physiology (such as cellular metabolism or redox rate) endoscopically in vivo, in situ and in real time with or without the use of foreign dyes. This will eliminate the need for tissue removal, histological tissue preparation and processing, thus reducing time and cost. Image-Guide Biopsy: The technology can be used for identifying suspicious areas associated with diseases such as cancer for target biopsy. This will reduce the false negative rate of random biopsy commonly used in clinical practice, and thus improve diagnosis yield. Surgical Guidance: The technology can be used for surgical guidance by delineating the normal and abnormal tissues in real time. Preterm Birth Risk Assessment: The technology can directly visualize cervical collagen fiber network and abnormal changes associated with preterm birth, providing a noninvasive means for assessing preterm birth risk. Preterm birth rate in the USA is about 12.7%, and preterm is the leading cause of neonate death. The associated annual healthcare cost is about 26 billion US dollars. The technology can also facilitate the development of therapeutics for treating or preventing preterm birth. Osteoarthritis Assessment: The technology can assess the cartilage integrity by directly visualizing the collagen fiber architecture when delivered to the articular space through a cannula. It can also be used to monitor the therapeutics effects on cartilage.

The portable, compact, fiber-optic endomicroscopy system can also be used as an affordable basic research tool, which is much cheaper than a bench-top microscope (by 100-200 fold cost reduction at least). It can be used for monitoring cell or tissue growth, imaging neuron function (by directly mounting on the head of live or even awake or freely-walking/behaving animals), and for studying infectious diseases (for which the endomicroscope will be in direct contact with infectious samples while other expensive equipment such as the laser and electronics can stay outside the barrier wall).

It should be noted that the computer application is programmed onto a non-transitory computer readable medium that can be read and executed by any of the computing devices mentioned in this application. The non-transitory computer readable medium can take any suitable form known to one of skill in the art. The non-transitory computer readable medium is understood to be any article of manufacture readable by a computer. Such non-transitory computer readable media includes, but is not limited to, magnetic media, such as floppy disk, flexible disk, hard disk, reel-to-reel tape, cartridge tape, cassette tapes or cards, optical media such as CD-ROM, DVD, Blu-ray, writable compact discs, magneto-optical media in disc, tape, or card form, and paper media such as punch cards or paper tape. Alternately, the program for executing the method and algorithms of the present invention can reside on a remote server or other networked device. Any databases associated with the present invention can be housed on a central computing device, server(s), in cloud storage, or any other suitable means known to or conceivable by one of skill in the art. All of the information associated with the application is transmitted either wired or wirelessly over a network, via the internet, cellular telephone network, RFID, or any other suitable data transmission means known to or conceivable by one of skill in the art.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A device comprising:
   a housing;
   a single-fiber light guide configured for delivery of excitation light and collection of emission light disposed within the housing;
   a phase diffractive grating;
   a piezoelectric tube (PZT) configured to function as an actuator disposed at a first end of the housing; and
   an achromatic objective lens disposed at a second end of the housing.

2. The device of claim 1 wherein the single-fiber light guide comprises a single double-clad optical fiber.

3. The device of claim 1 wherein the single-fiber light guide comprises a single or multiple single-mode cores and multiple claddings, with the core(s) for delivery of excitation light to the sample, and at least one cladding (and the core(s)) for collection of emission light from the sample.

4. The device of claim 1 wherein the single-fiber light guide comprises one selected from a group consisting of a pure silica core, a potassium doped silica core, and a hollow core.

5. The device of claim 1 wherein the single-fiber light guide comprises an optical fiber having at least one single-mode core and one cladding also including a low refractive index coating.

6. The device of claim 1 wherein the objective lens comprises low or no chromatic aberration and configured to have a wavelength range of interest to improve the efficiency of coupling the emission light back into the single-fiber light guide.

7. The device of claim 1 wherein the achromatic objective lens is configured for collecting the emission light with a short wavelength between 350 nm and 600 nm mainly generated from the focal volume of the excitation light of a long wavelength between 750 nm and 1060 nm.

8. The device of claim 1 wherein the achromatic objective lens comprises a miniature compound lens further comprising multi-elements of different refractive index profiles (including GRIN lenses/glasses) and/or curvatures to correct chromatic aberration and field flatness for a scanning input imaging beam.

9. The device of claim 1 wherein the achromatic objective lens comprises a miniature compound lens with a diffraction element/mask to compensate the chromatic aberration and thus reduce the longitudinal focal shift, while maintaining a high numerical aperture (and thus resolution).

10. The device of claim 1 further comprising a built-in mechanism to perform 2D and 3D beam scanning.

11. The device of claim 10 wherein the built-in mechanism to perform 2D and 3D beam scanning comprises one selected from a group consisting of a PZT actuated 2D fiber scanner, an MEMS actuated 2D or 3D fiber scanner, a built-in depth scanner, and a mechanical scanner consisting of a compressed spring and shape-memory alloy wires to translate parts of the focusing optics relative to the rest of the probe.

12. The device of claim 10 wherein the built-in mechanism is equipped with corresponding drive and control electronics.

13. The device of claim 1 further comprising a short pulsed light source as the excitation light source.

14. The device of claim 1 further comprising a dispersion management unit configured to compensate the dispersion of the single-fiber light guide and other optics in the system to achieve short pulses and predetermined emission signal production.

15. The device of claim 14 wherein the dispersion management unit comprises one selected from a group consisting of a photonic bandgap fiber, a pair of gratings, a pair of prisms, and a grating-lens pair.

16. The device of claim 1 further comprising a mechanism to separate the emission light from the excitation light.

17. The device of claim 16 wherein the mechanism to separate the emission light from the excitation light comprises a dichroic mirror.

18. The device of claim 1 further comprising a light detector configured to detect the emission light, electronics to condition and acquire the signal, and electronics to digitize and store the signal in digital form.

19. The device of claim 18 wherein the light detector comprises a photomultiplier tube.

20. The device of claim 1 further comprising a control device, imaging beam scanner drive, data acquisition, display and storage unit to control and synchronize the drive signals and data acquisition, digitize the data, process the data, and store data.

21. The device of claim 1 further comprising optics configured to couple the light between free space and single-fiber light guide.

* * * * *